US00PP16496P3

(12) United States Plant Patent
McGranahan et al.

(10) Patent No.: US PP16,496 P3
(45) Date of Patent: May 2, 2006

(54) WALNUT TREE NAMED 'SEXTON'

(50) Latin Name: *Juglans regia*
Varietal Denomination: Sexton

(75) Inventors: Gale McGranahan, Davis, CA (US); Charles Leslie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 63 days.

(21) Appl. No.: 10/943,371

(22) Filed: Sep. 17, 2004

(65) Prior Publication Data

US 2006/0031971 P1 Feb. 9, 2006

Related U.S. Application Data

(63) Continuation-in-part of application No. 10/912,852, filed on Aug. 6, 2004, now abandoned.

(51) Int. Cl.
*A01H 5/00* (2006.01)

(52) U.S. Cl. ..... Plt./154

(58) Field of Classification Search ..... Plt./154
See application file for complete search history.

*Primary Examiner*—Anne Marie Grunberg
*Assistant Examiner*—June Hwu
(74) *Attorney, Agent, or Firm*—Morrison & Foerster LLP

(57) ABSTRACT

A new and distinct variety of walnut tree denominated 'Sexton' is described. This new cultivar comes into bearing young and produces well mid-season. It bears a jumbo sized nut with a strong, well filled shell which is easily removed and contains light to extra light colored kernels with little size variation in a given harvest. The new tree also shows low susceptibility to walnut blight.

7 Drawing Sheets

FIELD OF THE INVENTION

Botanical/commercial classification: (*Juglans regia*)/new English walnut variety. Varietal denomination: cv. Sexton.

BACKGROUND OF THE INVENTION

The present invention relates to a new and distinct variety of walnut tree *Juglans regia* which has been denominated varietally as 'Sexton,' and more particularly to such a walnut tree which has a harvest date approximately one week earlier than the walnut tree variety 'Chandler' (U.S. Plant Pat. No. 4,388) and which further produces a walnut that is jumbo in size with a smooth, tan colored shell, and light colored kernels which can be processed in shell or cracked.

It has long been recognized as desirable to provide walnut trees bearing large crops which are ripe for commercial harvesting and shipment midseason and exhibit low susceptibility to walnut blight. The tree of the present variety, 'Sexton,' produces a nut which is similar in some respects to common walnut tree varieties such as 'Chandler,' (U.S. Plant Pat. No. 4,388) and 'Tulare' (U.S. Plant Pat. No. 8,268). However the new variety is ready for harvest approximately one week before 'Chandler,' and two weeks after the common reference cultivar 'Payne' (not patented).

The new *Juglans regia* walnut tree of the present invention was created at Davis, Calif. in 1990 by a controlled cross of the cultivar 'Chandler' (U.S. Plant Pat. No. 4,388) and UC 85-8 (not patented). The pedigree is illustrated (FIG. 1). UC85-8 is a germplasm introduction which originated in the Xinjiang Province of China, and was provided by Xi, Sheng ke, Chinese Academy of Forestry, Beijing.

Seeds from the cross were planted and the resulting 31 trees were carefully observed along with other trees in the walnut breeding program. When they began to bear nuts, data were collected annually on leafing date, first peak and last female flower bloom, first, peak and last male bloom, blight severity and yield (Table 1). Nuts were sampled, cracked, and data was collected on shell appearance, shell thickness, shell integrity, shell strength, nut weight, kernel weight, percent kernel, ease of kernel removal, kernel color, and percent kernel shrivel (Table 2). A single tree was selected from among progeny of this controlled cross based on its superior attributes. This selection was originally designated 'UC90-31-10,' and is now designated the 'Sexton' cultivar after Joseph Sexton, a historical figure said be responsible for the soft shell walnut industry in Southern California. 'Sexton' was originally asexually reproduced by grafting in Davis, Calif., Parlier, Calif., and Chico, Calif. 'Sexton' is stable and reproduces true to type.

SUMMARY OF THE INVENTION

It was found that the new *Juglans regia* of the present invention exhibits the following combination of characteristics:

a) Comes into bearing young, at age 3 years;
b) forms jumbo-sized walnuts that possess strong well-filled shells and easy to remove light-colored kernels with little size variation in a given harvest;
c) can be processed inshell or cracked;
d) bears fruit laterally;
e) yields a walnut crop that can be harvested in the middle of the harvest season and prior to 'Chandler' (U.S. Plant Pat. No. 4,388);
f) and exhibits low susceptibility to blight.

BRIEF DESCRIPTION OF THE TABLES

Table 1 shows comparative tree evaluations.

Table 2 shows nut and kernel traits.

BOTANICAL DESCRIPTION OF THE PLANT

The description is based on an ungrafted walnut on its own roots and trees propagated by grafting on Paradox rootstock and growing in an orchard at Davis, Calif. Data were collected on the own rooted tree from 1994, age 3 years, to 2003, age 12 years. In 2000, scionwood from this tree was collected and grafted onto Paradox rootstock for further evaluation in three sites: Davis, Chico and Kearney. Data is summarized in Tables 1 and 2.

The Munsell Book of Color is used in the identification of color. Also, common color terms are to be accorded their ordinary dictionary significance.

Botanical classification: *Juglans regia.*

*Female parent.*—'Chandler' (U.S. Plant Pat. No. 4,388).

*Male parent.*—UC85-8 (non-patented in the United States).

Figure 1:
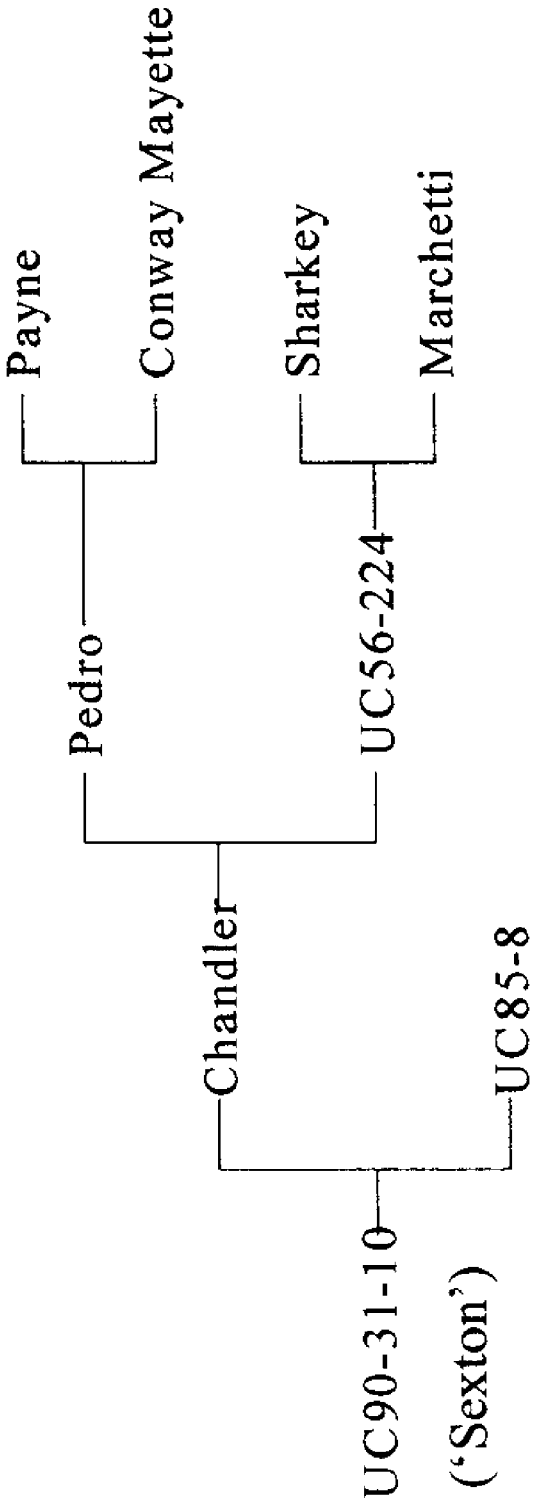
FIG. 1—shows the pedigree of the 'Sexton' walnut.

The pedigree is shown (FIG. 1). 'Sexton' differs from its male parent UC85-8 in having lighter colored kernels and less tendency to have "second blooms" which is commercially undesirable. It is also a smaller tree and has a phenology between its two parents.

Figure 2:
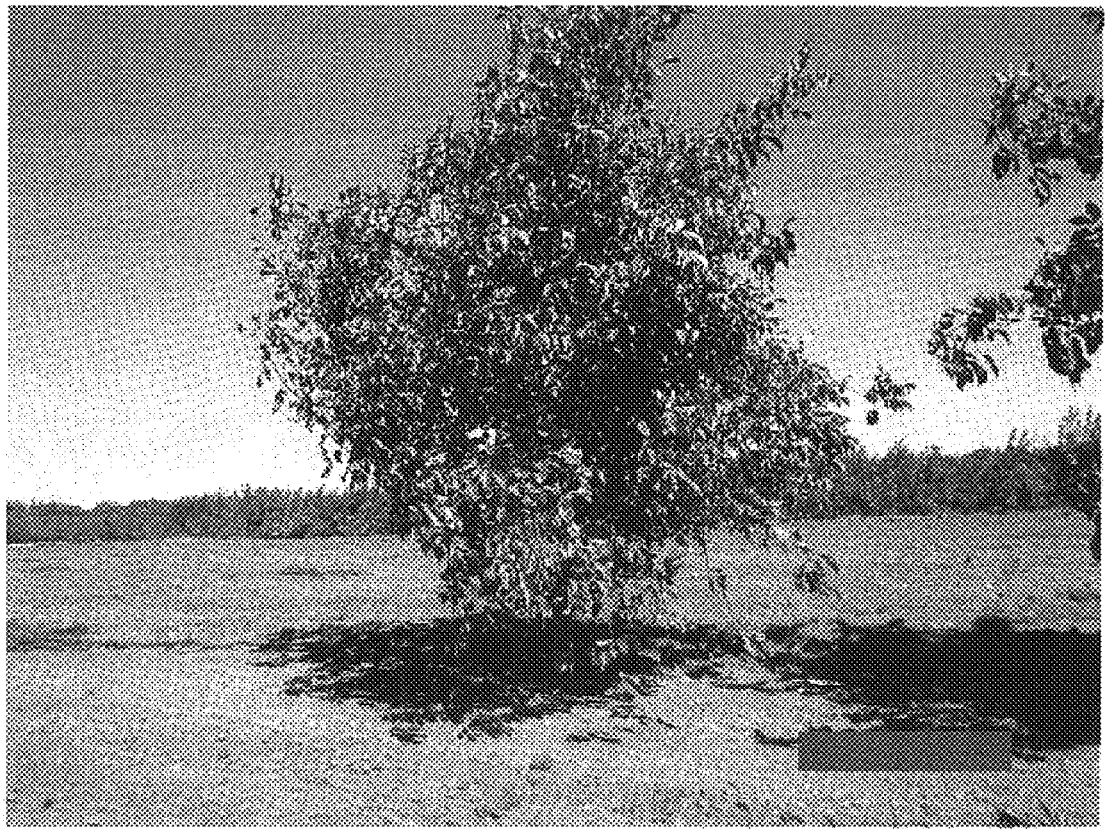
FIG. 2—shows a tree of the 'Sexton' walnut at 12 years of age.
Figure 3:
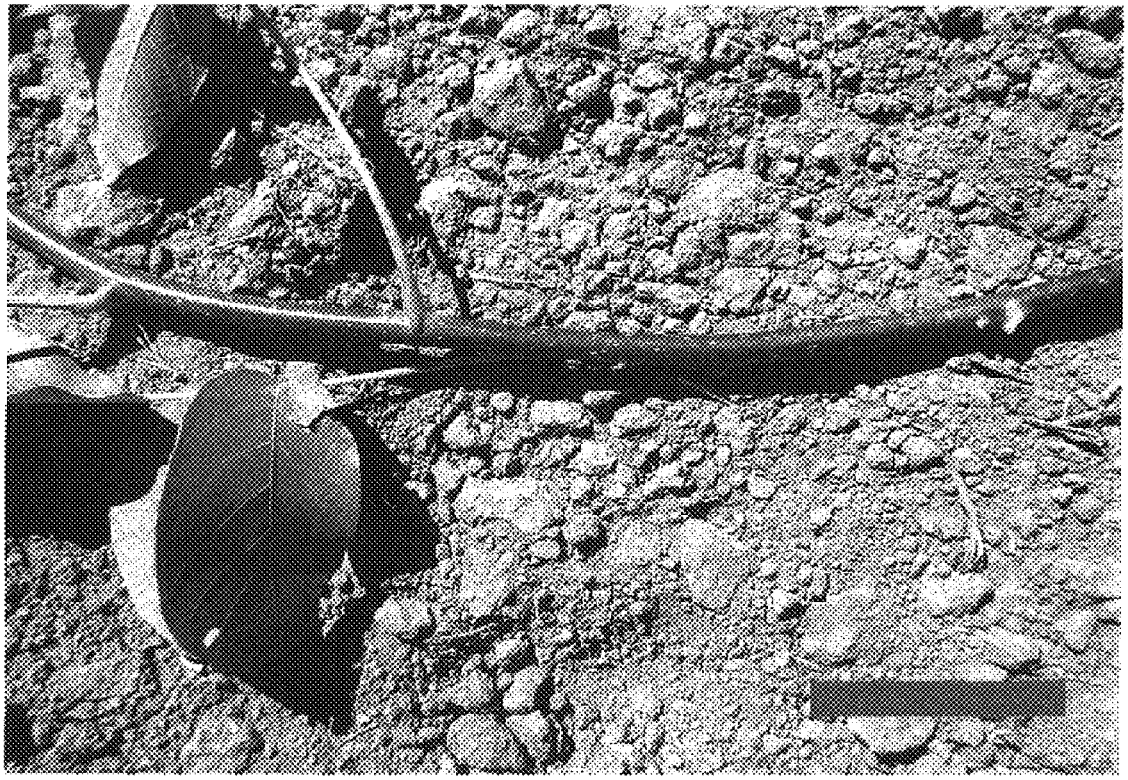
FIG. 3—shows a near view of the typical current season's stem of the 'Sexton' walnut.
Figure 5:
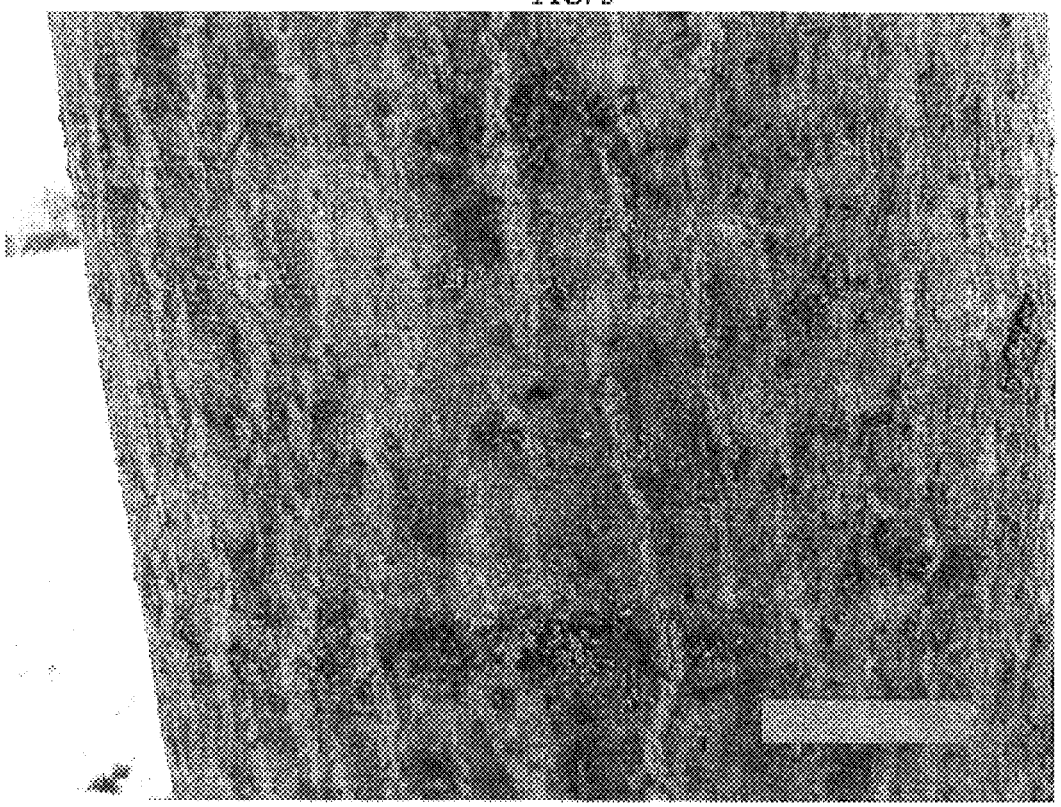
FIG. 5—shows a near view of the bark of the 'Sexton' walnut.
Figure 6:
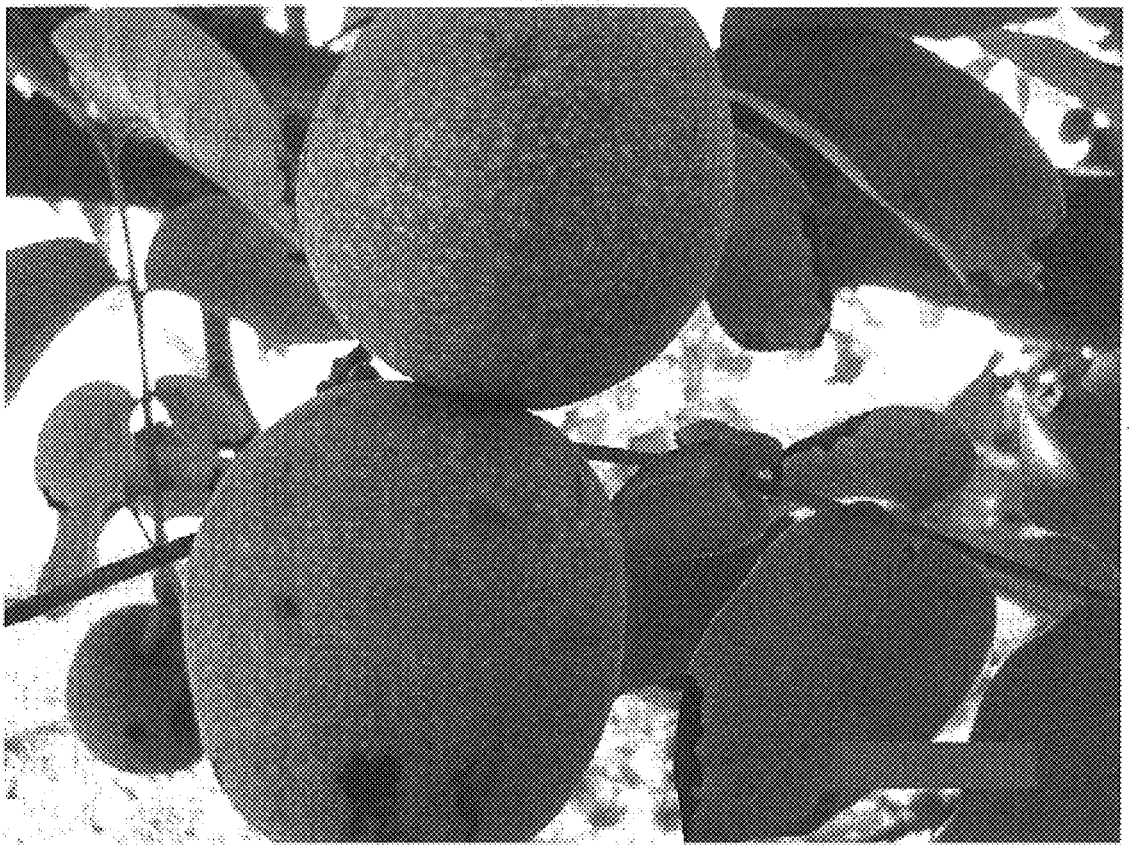
FIG. 6—shows nuts in the hull of the 'Sexton' walnut.
Figure 7:
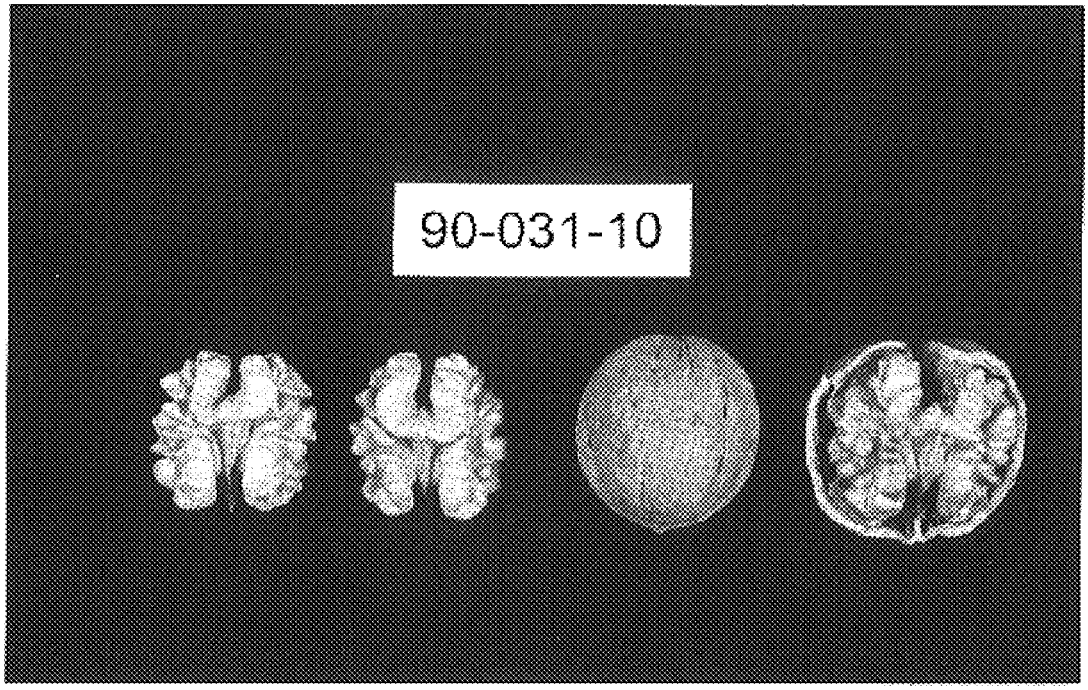
FIG. 7—shows nuts and kernels of the 'Sexton' walnut.

Plant: The growth habit of the tree is illustrated in FIG. 2. This 12 year old tree was approximately 15 feet in height with a canopy diameter of approximately 17 feet. The trunk diameter at 30 cm above the ground is approximately 25 cm. The silver grey bark (as illustrated) is typical of *Juglans regia.* The young bark is brown (8.0YR 3.0/5.4) with numerous raised lenticels (FIG. 3) 'Sexton''s lenticels are oval, measure 2–10 mm by 1–2 mm and are light grey yellow brown (9.7YR 4.6/2.1). 'Sexton''s bark color is yellow grey (3.8Y 7.4/1.4) with lighter brown-grey striations (7.0YR 5.4/1.2) (FIG. 5). On one to two year old bark there are about 32 lenticels per 2.5 cm of stem measuring approximately 1.5 cm in diameter. 'Sexton' has less than average vigor and is comparable to the variety 'Howard'. The surface texture of the trunk, branch, leaflets, hull and kernel is smooth.

Figure 4:
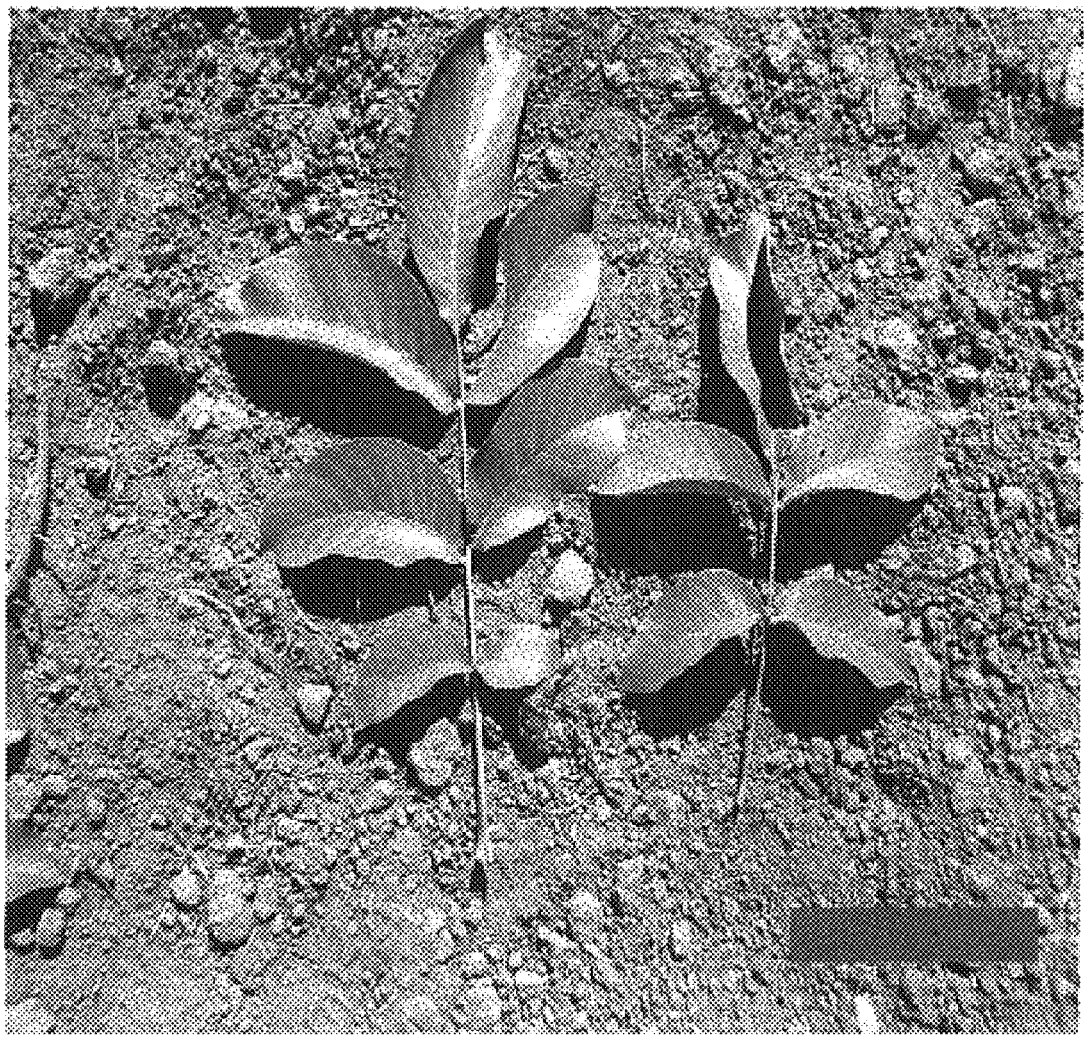
FIG. 4—shows a near view of the leaves of the 'Sexton' walnut.

Foliage: The dark green foliage is illustrated (FIG. 4) and is typical of *Juglans regia.* Leaf out during 1994–2003 has occurred on March 29 on the average. For comparative purposes the 'Payne' cultivar leafed out 11 days earlier and the 'Chandler' cultivar leafed out 6 days later during the same years. The typical leaf coloration is green, 8.2GY 3.2/6.1, on the upper surface and slightly lighter (5.3GY 5.2/9.7) on the lower surface. The leaves are pinnately compound with 5–7 leaflets. The full leaf length is approximately 38 cm and the width 28 cm. The terminal leaflet averages 15.6 cm in length and 9.5 cm in width. The middle leaflets average 14 cm in length and 6.6 cm in width and the proximal leaflets average 12.1 cm in length and 6.2 cm in width. If 7 leaflets are present the first (proximal) set is smallest averaging 9.6 cm in length and 5.7 cm in width. The leaflets are broadly elliptical and entire. The petiole averages 24 cm in length and is 2–4 mm in diameter. The entire rachis including the petiole is 24 cm in length, 2–4 mm in diameter and the distance to the first leaflet (petiole) is 7 cm. The color is yellow-green 5GY 6/8.

Inflorescence: The tree is relatively precocious, first female flowers being noted at age 3 years. Male flowers (catkins) were not present until age 5 years. This delay in male maturity is typical of *Juglans regia.* From 1994 to 2002 first female bloom occurred on an average on April 9, peak bloom on April 13 and last bloom on April 19. From 1996 to 2002 average male flowering (pollen shedding) began April 4, peaked on April 8 and terminated April 17. In this protandrous tree, pollen shedding does not completely cover pistillate bloom suggesting that a pollenizer would be needed for maximum yield in isolated areas. Both 'Tulare' and 'Chandler' would be satisfactory pollenizers. The female flowers are typical of *Juglans regia* with two flowers per inflorescence borne at both terminal and lateral positions on current season's growth. Approximately 100% of the lateral buds contain inflorescences making yields much greater than trees that only bear flowers terminally. A typical female flower is approximately 5 to 7 mm at anthesis and the floral organs are typical of *J. regia.* The flower fragrance is typical of *J. regia* and is not noticeably different than the foliage fragrance. The flowers are typical of the species appearing vase shaped when the two plumose stigmatic arms are curved outwardly. There are no petals. The flowers measure 5–7 mm in length and 3–5 mm in diameter and are yellow-green (5GY 6/8) in color. They are borne usually in twos on a 1 cm spike. The male flowers are plentiful and measure about 8.5 cm in length. The catkin's diameter is about 15 mm and yellow-green (5GY 6/8). Catkin length ranges between 7 and 13 cm, averaging 8.5 cm.

Walnuts: The new cultivar commonly harvests at least one week before 'Chandler' and two weeks after 'Payne' but may become earlier as the clone ages. During 2002, nuts of this new cultivar were ready for harvest on October 3. This compares with 'Payne' which harvested September 17 and 'Chandler' that harvested October 8. The new cultivar has excellent yields of jumbo sized walnuts. The hull is globose, moderate yellow-green (5GY 5/6), measures 4.7 cm long and 5.2 cm wide and is 4.3 mm thick. The almost round nutshell is tan, smooth, and measures approximately 37.9 mm in length and 37.1 mm in width. The nut's basal and apex shape is rounded with a slight tip at the apex. The color is light brown (2Y 5/6). The shell is strong and well sealed and the kernel is easy to remove. The kernel weighs 8.5 g and makes up 51.8% of the total nut weight of 16.4 g. Kernel color is considered excellent and scores mostly in the light to extra light categories of the USDA Standards for Grades of Shelled Walnuts as determined by using the standard Walnut Color Chart for kernels published by the Dried Fruit Association of California. In addition kernels of 'Sexton' scored 52.2 on the Relative Light Index used by Diamond Walnut of Stockton, Calif. The kernels do not have a shiny surface like the 'Chandler' walnut does. These values are based on 9 year averages of ten walnut samples obtained from a young tree. Typical kernel dimensions are approximately 31.9 mm in length and 30.5 mm in width. The kernel is essentially round and splits into halves easily. It is plump in comparison to 'Chandler'. It is typical of commercial walnuts in terms of flavor and firmness, the latter varying according to the percent moisture after drying.

Hardiness: Trees have withstood temperatures of 21° F. in 1998.

Chilling requirement: Trees exhibited staggered leafing and bloom, symptoms of lack of chilling in 1998, a year when chilling hour accumulation (hours under 45° F.) were 717. This was not noted when chilling hour accumulation was over 800.

Disease resistance and susceptibility: Susceptibility to walnut blight has been low. No other unusual resistance or susceptibility to insects and diseases has been observed to date.

Usage: The new cultivar of the present invention provides an early harvesting walnut cultivar with light colored kernels that can be used cracked or in shell.

TABLE 1

TREE EVALUATIONS

| | Leafing date | DAP L | Male bloom date | DAP M | Female bloom date | DAP F | Harvest Date | DAP H |
|---|---|---|---|---|---|---|---|---|
| 1999 | | | | | | | | |
| Payne | 3/24 | 0 | 4/14 | 0 | 4/18 | 0 | 9/24 | 0 |
| Tulare | 4/10 | 17 | 4/17 | 3 | 4/25 | 7 | 10/5 | 11 |
| Chandler | 4/13 | 20 | 4/17 | 3 | 4/28 | 10 | 10/19 | 25 |
| Sexton | 4/6 | 13 | 4/18 | 4 | 4/19 | 1 | 10/1 | 7 |
| Gillet | 4/11 | 18 | | | 4/22 | 4 | 10/10 | 16 |
| Forde | 4/14 | 21 | | | 4/23 | 5 | 10/22 | 28 |
| 2000 | | | | | | | | |
| Payne | 3/19 | 0 | 3/31 | 0 | 4/5 | 0 | 9/13 | 0 |
| Tulare | 4/3 | 15 | 4/11 | 11 | 4/16 | 10 | 10/3 | 20 |
| Chandler | 4/4 | 16 | 4/12 | 12 | 4/20 | 15 | 10/12 | 29 |
| Sexton | 3/28 | 9 | 4/5 | 5 | 4/10 | 5 | 9/30 | 17 |
| Gillet | 3/30 | 11 | | | 4/7 | 2 | 9/26 | 13 |
| Forde | 4/3 | 15 | | | 4/10 | 5 | 10/7 | 24 |
| 2001 | | | | | | | | |
| Payne | 3/17 | 0 | 3/27 | 0 | 4/1 | 0 | 9/9 | 0 |
| Tulare | 3/29 | 12 | 4/10 | 13 | 4/20 | 20 | 9/27 | 15 |
| Chandler | 3/29 | 12 | 4/10 | 13 | 4/23 | 22 | 10/7 | 28 |
| Sexton | 3/22 | 5 | 3/26 | 0 | 4/7 | 6 | 9/29 | 20 |
| Gillet | 3/23 | 6 | 4/15 | 18 | 3/30 | −2 | 9/18 | 9 |
| Forde | 3/24 | 7 | 4/15 | 18 | 4/3 | 2 | 9/29 | 20 |
| 2002 | | | | | | | | |
| Payne | 3/27 | 0 | 4/6 | 0 | 4/12 | 0 | 9/18 | 0 |
| Tulare | 4/6 | 10 | 4/15 | 9 | 4/24 | 12 | 10/3 | 16 |
| Chandler | 4/7 | 11 | 4/17 | 11 | 4/27 | 15 | 10/9 | 21 |
| Sexton | 4/1 | 5 | 4/10 | 4 | 4/15 | 3 | 10/3 | 15 |
| Gillet | 4/1 | 5 | 4/23 | 17 | 4/11 | −1 | 10/4 | 16 |
| Forde | 4/2 | 6 | 4/23 | 17 | 4/13 | 1 | 10/6 | 18 |
| 2003 | | | | | | | | |
| Payne | 3/18 | 0 | 4/5 | 0 | 4/9 | 0 | 9/21 | 0 |
| Tulare | 4/5 | 18 | 4/18 | 13 | 4/26 | 17 | 10/5 | 14 |
| Chandler | 4/7 | 20 | 4/20 | 15 | 5/3 | 25 | 10/10 | 19 |
| Sexton | 3/24 | 6 | 4/5 | 0 | 4/9 | 0 | 10/6 | 15 |
| Gillet | 3/24 | 6 | 4/18 | 13 | 4/4 | −5 | 10/1 | 10 |
| Forde | 3/27 | 9 | 4/23 | 18 | 4/9 | 0 | 10/3 | 12 |
| 5 YEAR AVERAGE | | | | | | | | |
| Payne | 3/21 | 0 | 4/4 | 0 | 4/9 | 0 | 9/17 | 0 |
| Tulare | 4/4 | 14 | 4/14 | 10 | 4/22 | 13 | 10/3 | 17 |
| Chandler | 4/7 | 16 | 4/15 | 11 | 4/26 | 17 | 10/11 | 24 |
| Sexton | 3/29 | 8 | 4/6 | 2 | 4/12 | 3 | 10/1 | 15 |
| Gillet | 3/30 | 9 | 4/19 | 16 | 4/8 | 0 | 9/30 | 13 |
| Forde | 4/1 | 11 | 4/20 | 18 | 4/12 | 3 | 10/7 | 20 |

TABLE 1-continued

TREE EVALUATIONS

| | Season length | Overlap % | Male abundance | Female abundance | Lateral fruitfulness % | Yield | Blight |
|---|---|---|---|---|---|---|---|
| 1999 | | | | | | | |
| Payne | 159 | 89 | 6 | 7 | 100 | 6 | 3 |
| Tulare | 166 | 27 | 4 | 6 | 90 | 6 | 0 |
| Chandler | 174 | 53 | 4 | 5 | 90 | 5 | 3 |
| Sexton | 165 | 88 | 6 | 7 | 100 | 7 | 2 |
| Gillet | 171 | | | 5 | 90 | 5 | 0 |
| Forde | 182 | | | 6 | 100 | 4 | 0 |
| 2000 | | | | | | | |
| Payne | 161 | 89 | 6 | 6 | 100 | 6 | 5 |
| Tulare | 172 | 100 | 6 | 6 | 100 | 6 | 4 |
| Chandler | 175 | 67 | 4 | 5 | 90 | 4 | 0 |
| Sexton | 173 | 54 | 5 | 6 | 100 | 6 | 0 |
| Gillet | 172 | | | 6 | 100 | 6 | 0 |
| Forde | 180 | | | 5 | 100 | 6 | 0 |
| 2001 | | | | | | | |
| Payne | 161 | 89 | 7 | 6 | 100 | 5 | 8 |
| Tulare | 160 | 85 | 6 | 6 | 70 | 5 | 3 |
| Chandler | 167 | 38 | 5 | 5 | 100 | 4 | 2 |
| Sexton | 175 | 53 | 5 | 6 | 100 | 6 | 1 |
| Gillet | 172 | | 3 | 6 | 100 | 7 | 0 |
| Forde | 179 | | 2 | 6 | 100 | 7 | 0 |
| 2002 | | | | | | | |
| Payne | 159 | 60 | 7 | 6 | 100 | 7 | 3 |
| Tulare | 162 | 91 | 5 | 6 | 100 | 6 | 0 |
| Chandler | 165 | 75 | 5 | 6 | 100 | 6 | 1 |
| Sexton | 171 | 83 | 6 | 6 | 100 | 6 | 0 |
| Gillet | 176 | 40 | 4 | 6 | 100 | 6 | 0 |
| Forde | 176 | 11 | 4 | 6 | 100 | 6 | 0 |
| 2003 | | | | | | | |
| Payne | 165 | 62 | 5 | 6 | 100 | 6 | 7 |
| Tulare | 164 | 92 | 5 | 6 | 100 | 6 | 5 |
| Chandler | 160 | 50 | 4 | 6 | 100 | 4 | 0 |
| Sexton | 180 | 100 | 5 | 6 | 100 | 6 | 2 |
| Gillet | 180 | 42 | 6 | 6 | 100 | 7 | 1 |
| Forde | 177 | 20 | 4 | 6 | 100 | 7 | 2 |
| 5 YEAR AVERAGE | | | | | | | |
| Payne | 161 | 78 | 6.2 | 6.2 | 100 | 6 | 5.2 |
| Tulare | 165 | 79 | 5.2 | 6 | 92 | 5.8 | 2.4 |
| Chandler | 168 | 57 | 4.4 | 5.4 | 96 | 4.6 | 1.2 |
| Sexton | 173 | 76 | 5.4 | 6.2 | 100 | 6.2 | 1 |
| Gillet | 174 | 41 | 4.3 | 5.8 | 98 | 6.2 | 0.2 |
| Forde | 179 | 15 | 3.3 | 5.8 | 100 | 6 | 0.4 |

KEY TO TABLE 1

| | |
|---|---|
| Leafing date | Date when 50% of terminal buds have enlarged and the bud scales have split exposing the green leaves |
| DAP L | Days after Payne (reference cultivar) leafing |
| Male bloom date | Date when maximum pollen shedding occurs |
| DAP M | Days after Payne (reference cultivar) male bloom |
| Female bloom date | Date of maximum pistillate flower receptivity |
| DAP F | Days after Payne (reference cultivar) female bloom |
| Harvest Date | Date when 95% of the nuts separate from the hulls |
| DAP H | Days after Payne (reference cultivar) harvest |
| Season length | Days between female flowering and harvest |
| Overlap % | Percent of female bloom overlapped by male bloom |
| Male abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Blight | Blight incidence: 3 low; 5 intermediate; 7 high DFA Dried Fruit Association of CA |

TABLE 2

NUT AND KERNEL TRAITS

| | SHELL | | | | | | |
|---|---|---|---|---|---|---|---|
| | Texture | Color | Seal | Strength | Integrity | Thickness | Packing tissue |
| 1999 | | | | | | | |
| Payne | 5 | 5 | 5 | 5 | 7 | 1.3 | 5 |
| Tulare | 5 | 6 | 4 | 4 | 7 | 1.2 | 5 |

TABLE 2-continued

| NUT AND KERNEL TRAITS | | | | | | | |
|---|---|---|---|---|---|---|---|
| Chandler | 5 | 4 | 5 | 4 | 7 | 1.2 | 5 |
| Sexton | 5 | 5 | 6 | 6 | 7 | 1.5 | 5 |
| Gillet | 5 | 5 | 3 | 5 | 7 | 1.5 | 5 |
| Forde | 5 | 5 | 5 | 5 | 7 | 1.6 | 5 |
| 2000 | | | | | | | |
| Payne | 5 | 5 | 5 | 5 | 7 | 1.4 | 5 |
| Tulare | 6 | 6 | 4 | 5 | 7 | 1.3 | 5 |
| Chandler | 5 | 5 | 5 | 4 | 7 | 1.4 | 5 |
| Sexton | 4 | 6 | 5 | 6 | 7 | 1.7 | 5 |
| Gillet | 6 | 5 | 4 | 4 | 7 | 1.3 | 5 |
| Forde | 6 | 5 | 4 | 5 | 7 | 1.2 | 5 |
| 2001 | | | | | | | |
| Payne | 5 | 5 | 5 | 5 | 7 | 1.5 | 5 |
| Tulare | 5 | 6 | 5 | 4 | 7 | 1.3 | 5 |
| Chandler | 5 | 4 | 5 | 4 | 7 | 1.5 | 5 |
| Sexton | 4 | 5 | 5 | 5 | 7 | 1.6 | 5 |
| Gillet | 5 | 5 | 4 | 4 | 7 | 1.2 | 5 |
| Forde | 5 | 5 | 5 | 5 | 7 | 1.5 | 5 |
| 2002 | | | | | | | |
| Payne | 5 | 5 | 5 | 5 | 7 | 1.0 | 5 |
| Tulare | 5 | 5 | 5 | 4 | 7 | 1.2 | 5 |
| Chandler | 5 | 4 | 5 | 5 | 7 | 1.5 | 5 |
| Sexton | 4 | 5 | 5 | 5 | 7 | 1.4 | 5 |
| Gillet | 5 | 5 | 4 | 5 | 7 | 1.3 | 5 |
| Forde | 5 | 4 | 5 | 5 | 7 | 1.5 | 5 |
| 2003 | | | | | | | |
| Payne | 5 | 5 | 5 | 6 | 7 | 1.6 | 5 |
| Tulare | 5 | 6 | 5 | 4 | 7 | 1.2 | 5 |
| Chandler | 5 | 4 | 5 | 4 | 7 | 1.3 | 5 |
| Sexton | 4 | 5 | 5 | 5 | 7 | 1.5 | 5 |
| Gillet | 5 | 5 | 5 | 5 | 7 | 1.3 | 5 |
| Forde | 6 | 5 | 6 | 6 | 7 | 1.6 | 5 |
| 5 YEAR AVERAGE | | | | | | | |
| Payne | 5 | 5 | 5 | 5.2 | 7 | 1.4 | 5 |
| Tulare | 5.2 | 5.6 | 4.6 | 4.2 | 7 | 1.2 | 5 |
| Chandler | 5 | 4.2 | 5 | 4.2 | 7 | 1.4 | 5 |
| Sexton | 4.2 | 5.2 | 5.2 | 5.4 | 7 | 1.5 | 5 |
| Gillet | 5.2 | 5 | 4 | 4.6 | 7 | 1.3 | 5 |
| Forde | 5.4 | 4.8 | 5 | 5.2 | 7 | 1.5 | 5 |

| | | | | KERNEL | | | |
|---|---|---|---|---|---|---|---|
| | Inshell weight | Kernel weight | Kernel % | Fill | Plump-ness | Ease of removal | Blanks % |
| 1999 | | | | | | | |
| Payne | 16.9 | 5.3 | 44.9 | 5 | 4 | 4 | 0 |
| Tulare | 14.0 | 7.7 | 57.7 | 5 | 5 | 4 | 0 |
| Chandler | 13.7 | 7.1 | 52.2 | 4 | 5 | 3 | 0 |
| Sexton | 14.2 | 6.9 | 48.4 | 5 | 5 | 4 | 0 |
| Gillet | 16.5 | 8.2 | 49.8 | 5 | 4 | 5 | 0 |
| Forde | 18.6 | 9.7 | 51.7 | 5 | 6 | 5 | 0 |
| 2000 | | | | | | | |
| Payne | 12.8 | 6.1 | 48.0 | 5 | 5 | 4 | 0 |
| Tulare | 16.4 | 9.2 | 56.5 | 5 | 5 | 5 | 0 |
| Chandler | 13.7 | 6.7 | 49.1 | 5 | 4 | 4 | 0 |
| Sexton | 17.0 | 8.6 | 50.7 | 6 | 5 | 5 | 0 |
| Gillet | 17.0 | 9.0 | 52.9 | 5 | 4 | 5 | 0 |
| Forde | 17.3 | 10.3 | 58.8 | 5 | 6 | 4 | 0 |
| 2001 | | | | | | | |
| Payne | 15.4 | 7.4 | 48.2 | 5 | 5 | 5 | 0 |
| Tulare | 16.9 | 8.8 | 52.5 | 5 | 5 | 5 | 0 |
| Chandler | 15.0 | 7.5 | 49.7 | 4 | 4 | 4 | 0 |
| Sexton | 16.0 | 8.2 | 51.2 | 6 | 5 | 5 | 0 |
| Gillet | 15.0 | 8.1 | 63.6 | 5 | 4 | 5 | 0 |
| Forde | 15.1 | 8.0 | 53.0 | 5 | 5 | 5 | 0 |

TABLE 2-continued

| NUT AND KERNEL TRAITS | | | | | | | |
|---|---|---|---|---|---|---|---|
| 2002 | | | | | | | |
| Payne | 12.1 | 5.6 | 46.6 | 5 | 5 | 5 | 0 |
| Tulare | 15.0 | 6.2 | 55.0 | 5 | 5 | 5 | 0 |
| Chandler | 13.7 | 6.2 | 45.4 | 4 | 4 | 4 | 0 |
| Sexton | 18.5 | 9.9 | 53.4 | 6 | 6 | 5 | 0 |
| Gillet | 15.2 | 7.7 | 50.6 | 5 | 5 | 5 | 0 |
| Forde | 16.7 | 8.9 | 53.4 | 5 | 5 | 4 | 0 |
| 2003 | | | | | | | |
| Payne | 15.6 | 7.4 | 47.1 | 5 | 5 | 5 | 0 |
| Tulare | 15.2 | 6.5 | 55.9 | 6 | 5 | 4 | 10 |
| Chandler | 13.8 | 7.1 | 51.1 | 5 | 4 | 4 | 0 |
| Sexton | 15.4 | 7.7 | 50.2 | 5 | 5 | 5 | 0 |
| Gillet | 16.2 | 8.2 | 50.5 | 5 | 5 | 5 | 0 |
| Forde | 17.6 | 9.1 | 51.7 | 5 | 5 | 4 | 0 |
| 5 YEAR AVERAGE | | | | | | | |
| Payne | 14.6 | 6.4 | 47 | 5 | 4.8 | 4.6 | 0 |
| Tulare | 15.5 | 8.5 | 55.5 | 5.2 | 5 | 4.6 | 2 |
| Chandler | 14 | 6.9 | 49.5 | 4.4 | 4.2 | 3.6 | 0 |
| Sexton | 16.2 | 8.3 | 50.8 | 5.6 | 5 | 4.6 | 0 |
| Gillet | 16 | 8.2 | 51.6 | 5 | 4.4 | 5 | 0 |
| Forde | 17.1 | 9.2 | 53.7 | 5 | 5.4 | 4.4 | 0 |

| | KERNEL | | | | | | |
|---|---|---|---|---|---|---|---|
| | Extra light % | Light % | Light amber % | Amber % | Tip shrivel % | Other shrivel % | Veins % |
| 1999 | | | | | | | |
| Payne | 50 | 30 | 20 | 0 | 0 | 20 | 30 |
| Tulare | 0 | 100 | 0 | 0 | 0 | 0 | 0 |
| Chandler | 90 | 10 | 0 | 0 | 30 | 0 | 0 |
| Sexton | 100 | 0 | 0 | 0 | 20 | 0 | 0 |
| Gillet | 0 | 100 | 0 | 0 | 0 | 0 | 0 |
| Forde | 0 | 100 | 0 | 0 | 0 | 0 | 0 |
| 2000 | | | | | | | |
| Payne | 0 | 100 | 0 | 0 | 1 | 0 | 30 |
| Tulare | 0 | 100 | 0 | 0 | 1 | 0 | 0 |
| Chandler | 60 | 40 | 0 | 0 | 40 | 0 | 0 |
| Sexton | 0 | 80 | 20 | 0 | 10 | 0 | 10 |
| Gillet | 0 | 90 | 10 | 0 | 20 | 0 | 20 |
| Forde | 0 | 90 | 0 | 10 | 10 | 0 | 0 |
| 2001 | | | | | | | |
| Payne | 30 | 70 | 0 | 0 | 0 | 0 | 20 |
| Tulare | 0 | 100 | 0 | 0 | 20 | 0 | 0 |
| Chandler | 100 | 0 | 0 | 0 | 10 | 0 | 0 |
| Sexton | 40 | 80 | 0 | 0 | 10 | 0 | 10 |
| Gillet | 0 | 90 | 10 | 0 | 0 | 0 | 0 |
| Forde | 0 | 90 | 10 | 0 | 0 | 0 | 0 |
| 2002 | | | | | | | |
| Payne | 0 | 90 | 10 | 0 | 0 | 0 | 0 |
| Tulare | 0 | 100 | 0 | 0 | 0 | 0 | 0 |
| Chandler | 100 | 0 | 0 | 0 | 40 | 0 | 0 |
| Sexton | 50 | 50 | 0 | 0 | 0 | 0 | 0 |
| Gillet | 0 | 100 | 0 | 0 | 0 | 10 | 10 |
| Forde | 100 | 0 | 0 | 0 | 0 | 0 | 0 |
| 2003 | | | | | | | |
| Payne | 0 | 90 | 10 | 0 | 0 | 0 | 10 |
| Tulare | 33 | 67 | 0 | 0 | 0 | 0 | 0 |
| Chandler | 100 | 0 | 0 | 0 | 20 | 0 | 0 |
| Sexton | 40 | 40 | 20 | 0 | 20 | 20 | 0 |
| Gillet | 10 | 90 | 0 | 0 | 10 | 0 | 0 |
| Forde | 50 | 50 | 0 | 0 | 10 | 0 | 0 |
| 5 YEAR AVERAGE | | | | | | | |
| Payne | 16 | 76 | 8 | 0 | 0.2 | 4 | 18 |
| Tulare | 7 | 93 | 0 | 0 | 4 | 0 | 0 |
| Chandler | 90 | 10 | 0 | 0 | 28 | 0 | 0 |

TABLE 2-continued

| NUT AND KERNEL TRAITS | | | | | | | |
|---|---|---|---|---|---|---|---|
| Sexton | 46 | 46 | 6 | 0 | 12 | 4 | 4 |
| Gillet | 2 | 94 | 4 | 0 | 6 | 2 | 6 |
| Forde | 30 | 56 | 2 | 2 | 4 | 0 | 0 |

KEY FOR TABLE 2

| | |
|---|---|
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | gm |
| Kernel weight | gm |
| Kernel % | Kernel wt/ inshell wt × 100 |
| Fill | Kernel fill: 3 poor; 5 moderate; 7 well |

TABLE 2-continued

| NUT AND KERNEL TRAITS | |
|---|---|
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like Chandler |
| Other shrivel % | Percent of kernels with more substantial shrivel |
| Veins % | Percent of kernels with conspicuous veins |
| | DFA Dried Fruit Association of CA |

What we claim is:

1. A new and distinct variety of walnut tree substantially as shown and described herein.

* * * * *

WALNUT TREE NAMED 'SEXTON'